United States Patent
Fowler (10) Patent No.: US 12,016,124 B2
(45) Date of Patent: Jun. 18, 2024

(54) COATING FOR ELECTRICAL COMPONENTS OF SURGICAL DEVICES

(71) Applicant: Covidien LP, Mansfield, MA (US)

(72) Inventor: David N. Fowler, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 635 days.

(21) Appl. No.: 17/190,511

(22) Filed: Mar. 3, 2021

(65) Prior Publication Data

US 2021/0330341 A1  Oct. 28, 2021

Related U.S. Application Data

(60) Provisional application No. 63/015,773, filed on Apr. 27, 2020.

(51) Int. Cl.
*A61B 17/32* (2006.01)
*A61B 17/072* (2006.01)
(Continued)

(52) U.S. Cl.
CPC ....... *H05K 1/181* (2013.01); *A61B 17/07207* (2013.01); *A61B 2017/00017* (2013.01);
(Continued)

(58) Field of Classification Search
CPC .............. A61B 17/07207; A61B 17/32; A61B 2017/00017; A61B 2017/0046; A61B 2017/00473; A61B 2017/00477; A61B 2017/00486; A61B 2017/00831; A61B 2090/0813; A61B 17/068; A61B 17/1155; A61B 2017/00398; A61B 2017/00526; A61B 2017/00734; A61B 2090/064; H05K 1/181; H05K 2201/0162; H05K 2201/0191; H05K 2201/0195; H05K 2201/09872; H05K 3/282; H05K 3/284; H05K 3/285; H05K 1/185; H05K 2203/085; H05K 2203/086; H05K 2203/087; H05K 2203/095; H05K 2203/122;
(Continued)

(56) References Cited

U.S. PATENT DOCUMENTS 3,406,061 A * 10/1968 Metcalfe ............... G03G 9/12
101/401.1
3,487,455 A * 12/1969 Laurell ............... H01B 9/027
174/127
(Continued)

FOREIGN PATENT DOCUMENTS

WO  2019139841 A1  7/2019

OTHER PUBLICATIONS

Extended European Search Report issued in corresponding application, 21170609.8, dated Oct. 21, 2021 (8 pages).

*Primary Examiner* — Timothy J Thompson
*Assistant Examiner* — Guillermo J Egoavil
(74) *Attorney, Agent, or Firm* — Carter, DeLuca & Farrell LLP (57) ABSTRACT

Surgical devices include adapter assemblies which electrically and mechanically interconnect handles of electromechanical surgical devices to surgical loading units. Electrical components of the surgical devices are coated with a multilayer conformal coating which permits the devices to be sterilized in an autoclave without damaging the electrical components.

20 Claims, 6 Drawing Sheets

(51) Int. Cl.
  *H01L 23/10* (2006.01)
  *H05K 1/18* (2006.01)
  *H05K 5/02* (2006.01)
  *H05K 5/06* (2006.01)
  *A61B 17/00* (2006.01)
  *A61B 90/00* (2016.01)

(52) U.S. Cl.
  CPC ............... *A61B 2017/0046* (2013.01); *A61B 2017/00486* (2013.01); *A61B 2017/00831* (2013.01); *A61B 2090/0813* (2016.02); *H05K 2201/0162* (2013.01); *H05K 2201/0195* (2013.01)

(58) Field of Classification Search
  CPC ... H05K 2203/1322; H05K 2203/1338; H05K 5/023; H05K 5/0247; H05K 5/069; H05K 5/02; H05K 5/06; H01L 23/10
  USPC ........................................................ 174/260
  See application file for complete search history.

(56) References Cited

U.S. PATENT DOCUMENTS

| | | |
|---|---|---|
| 8,034,452 B2 | 10/2011 | Padiyath et al. |
| 10,410,962 B2 | 9/2019 | McMahon et al. |
| 2017/0018730 A1* | 1/2017 | Popp .................. H10K 50/814 |
| 2018/0222157 A1* | 8/2018 | Heng ..................... F42B 15/34 |
| 2018/0338383 A1* | 11/2018 | Sgroi, Jr. ................ H01L 23/10 |
| 2019/0037705 A1* | 1/2019 | Singh .................... H05K 1/181 |
| 2019/0090358 A1* | 3/2019 | Aresta .................... C23C 16/30 |
| 2019/0174636 A1 | 6/2019 | Sgroi, Jr. et al. |

* cited by examiner

FIG. 7 to about 10000 cps.
COATING FOR ELECTRICAL COMPONENTS OF SURGICAL DEVICES

CROSS REFERENCE TO RELATED APPLICATION

This application claims the benefit of the filing date of provisional U.S. Application No. 63/015,773, filed on Apr. 27, 2020.

BACKGROUND

The present disclosure relates to coatings for adapter assemblies used in surgical systems. More specifically, the present disclosure relates to coatings for adapter assemblies which electrically and mechanically interconnect electromechanical surgical devices and surgical loading units.

A number of surgical device manufacturers have developed product lines with proprietary drive systems for operating and/or manipulating electromechanical surgical devices. In many instances the electromechanical surgical devices include a handle assembly, which is reusable, and loading units that are selectively connected to the handle assembly prior to use and then disconnected from the handle assembly following use in order to be disposed of or, in some instances, sterilized for re-use.

Sterilization of these surgical devices is frequently conducted using an autoclave or similar device. Autoclaves use steam and high pressure to sterilize the surgical devices. The steam can damage sensitive electrical components used with the surgical devices, and residual moisture on the electrical components after the sterilization of the surgical device may interfere with the functioning of the electrical components.

SUMMARY

The present disclosure provides coatings for electrical assemblies within electromechanical surgical devices. In aspects, the present disclosure provides a hand-held electromechanical surgical device including a housing, a loading unit, and an adapter assembly connecting the housing and the loading unit, the adapter assembly including an electrical assembly coated with a multi-layer conformal coating. In some aspects, the electrical assembly is a printed circuit board, including a substrate, a plurality of conductive tracks present on at least one surface of the substrate, and at least one electrical component connected to at least one conductive track.

The electrical component can be a resistor, capacitor, transistor, diode, amplifier, relay, transformer, battery, fuse, integrated circuit, switch, LED, LED display, Piezo element, optoelectrical component, antenna, oscillator, or combinations thereof.

In aspects, the multi-layer conformal coating covers the plurality of conductive tracks, the at least one electrical component, and the surface of the substrate on which the plurality of conductive tracks and the at least one electrical component are located.

The multi-layer conformal coating has at least one inner layer formed of a first material having a first viscosity and at least one outer layer formed of a second material having a second viscosity higher than the first viscosity.

In aspects, the first material is a silicone having a viscosity from about 195 cps to about 400 cps.

In some aspects, the inner layer has a thickness from about 50 μm to about 200 μm.

In aspects, the second material is a room temperature vulcanizing silicone having a viscosity from about 3000 cps to about 10000 cps.

In some aspects, the outer layer has a thickness from about 300 μm to about 500 μm.

The multi-layer conformal coating has a thickness from about 350 μm to about 700 μm.

In other aspects, the disclosure provides a hand-held electromechanical surgical device including a housing, a loading unit, and an adapter assembly connecting the housing and the loading unit. The adapter assembly includes an electrical assembly, in aspects a printed circuit board including a substrate, a plurality of conductive tracks present on at least one surface of the substrate, and at least one electrical component connected to at least one conductive track. The electrical assembly also includes a multi-layer conformal coating covering the plurality of conductive tracks, the at least one electrical component, and the surface of the substrate on which the plurality of conductive tracks and the at least one electrical component are located.

In aspects, the multi-layer conformal coating has at least one inner layer formed of a first material including a silicone having a viscosity from about 195 cps to about 400 cps, and at least one outer layer formed of second material including a room temperature vulcanizing silicone having a viscosity from about 3000 cps to about 10000 cps.

In some aspects, the inner layer has a thickness from about 50 μm to about 200 μm, and the outer layer has a thickness from about 300 μm to about 500 μm.

In aspects, the multi-layer conformal coating has a thickness from about 350 μm to about 700 μm.

In yet other aspects, the present disclosure provides an adapter assembly for connecting a surgical loading unit configured to perform a function with a handle of a surgical device that is configured to actuate the loading unit. The adapter assembly includes an electrical assembly including a printed circuit board, the printed circuit board including a substrate, a plurality of conductive tracks present on at least one surface of the substrate, and at least one electrical component connected to at least one conductive track. The electrical assembly also includes a multi-layer conformal coating covering the plurality of conductive tracks, the at least one electrical component, and the surface of the substrate on which the plurality of conductive tracks and the at least one electrical component are located.

The multi-layer conformal coating has at least one inner layer formed of a first material having a first viscosity and at least one outer layer formed of a second material having a second viscosity higher than the first viscosity.

In aspects, the first material is a silicone having a viscosity from about 195 cps to about 400 cps.

In some aspects, the inner layer has a thickness from about 50 μm to about 200 μm.

In aspects, the second material is a room temperature vulcanizing silicone having a viscosity from about 3000 cps to about 10000 cps.

In some aspects, the outer layer has a thickness from about 300 μm to about 500 μm.

In other aspects, the multi-layer conformal coating has a thickness from about 350 μm to about 700 μm.

BRIEF DESCRIPTION OF THE DRAWINGS

Various aspects of the disclosed surgical devices are described herein below with reference to the drawings, wherein.

DETAILED DESCRIPTION

The disclosed surgical devices are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

The presently disclosed surgical devices include an adapter assembly connecting a handle of a surgical device with an end effector of the surgical device. The adapter assembly includes an electrical assembly therein which possesses electrical components that transmit electrical signals between the handle and the end effector.

An exemplary electrical assembly is a printed circuit board ("PCB"), and its components. A PCB generally includes a substrate formed of an insulating material, a plurality of conductive tracks present on at least one surface of the substrate, and at least one electrical component connected to at least one conductive track.

Suitable electrical components of the electrical assembly include any circuit element. For example, the electrical component can be a resistor, capacitor, transistor, diode, amplifier, relay, transformer, battery, fuse, integrated circuit, switch, LED, LED display, Piezo element, optoelectrical component, antenna and/or oscillator. Any suitable number and/or combination of electrical components may be connected to the electrical assembly.

At least a portion of the electrical assembly, including the electrical components present in the disclosed surgical devices, has a coating which is resistant to the heat, moisture and pressure used when sterilizing the surgical devices with an autoclave. In aspects, the coating is a multi-layer conformal coating on at least one surface of the electrical assembly. The multi-layer conformal coating is a thin and flexible layer that conforms to the contours of any electrical assembly within the surgical device. In aspects, the multi-layer conformal coating covers the plurality of conductive tracks, the at least one electrical component, and the surface of the substrate on which the plurality of conductive tracks and the at least one electrical component are located.

Materials used to form the multi-layer conformal coating are within the purview of those skilled in the art. There are 5 main classes of conformal coatings, based upon the materials used to form the coating: AR (acrylic); ER (epoxy); SR (silicones); UR (urethanes); and XY (paraxylenes).

In aspects, the inner layer of the multi-layer conformal coating is formed of a low viscosity material (sometimes referred to herein as "a first material having a first viscosity"), which can wick around and beneath the electrical component mounted on a surface of the PCB. Because of its low viscosity, the material used to form the inner layer component may not adequately coat (due to gravity and other external forces) the surface of taller electrical components projecting from the surface of the PCB (in some cases by more than about 0.050 inches (1270 μm)), including certain resistors and capacitors.

The outer layer of the multi-layer conformal coating, formed of a high viscosity material (sometimes referred to herein as "a second material having a second viscosity higher than the first viscosity"), does not wick around and beneath the components which the low viscosity material forming the inner layer has already coated. The outer layer coats the taller electrical components projecting from the surface of the PCB and remains adhered thereto, thus providing protection to those electrical components.

Suitable low viscosity materials which may be used to form the inner layer of the multi-layer conformal coating include silicone materials. Exemplary silicones include those commercially available as Humiseal 1C55 (commercially available from Chase Corporation (Westwood, MA)). The low viscosity material may have a viscosity from about 195 cps to about 400 cps, in aspects from about 225 cps to about 350 cps.

The low viscosity material may be applied by dipping, brushing, spraying, plasma deposition, combinations thereof, and the like. After application, the low viscosity material is cured as necessary to form the inner layer of the multi-layer conformal coating. Curing may occur by exposure to air, elevated temperatures in an oven (batch or continuous), UV curing, combinations thereof, and the like. In aspects, the low viscosity material may be heated to cure. The temperatures and times for heating will depend on a variety of factors, including the characteristics of the electrical components being coated, the oven or similar machinery used to cure the material, as well as the loading of the components in the oven (batch vs. continuous), and the like.

In aspects, multiple applications of the low viscosity material forming the inner layer may be applied to the electrical assembly, so the inner layer, itself, is formed of multiple layers.

The thickness of the inner layer may be from about 50 μm to about 200 μm, in aspects from about 70 μm to about 180 μm.

Suitable high viscosity materials which may be used to form the outer layer of the multi-layer conformal coating include room temperature vulcanizing (RTV) silicone materials. Exemplary RTV silicone materials include any combination of silica, silanes, and/or siloxanes, or the like. Exemplary high viscosity materials include those commercially available as M-Coat C, (commercially available from Vishay Measurements Group, Inc. (Raleigh, NC)). The high viscosity material may have a viscosity from about 3000 cps to about 10000 cps, in aspects from about 4000 cps to about 9000 cps.

The high viscosity material may be applied by dipping, brushing, spraying, plasma deposition, combinations thereof, and the like. After application, the high viscosity material is cured as necessary to form the outer layer of the multi-layer conformal coating. Curing may occur by exposure to air, elevated temperatures in an oven (batch or continuous), UV curing, combinations thereof, and the like. In aspects, the high viscosity material may be heated to cure. The temperatures and times for heating will depend on a variety of factors, including the characteristics of the electrical components being coated, the oven or similar machinery used to cure the material, as well as the loading of the components in the oven (batch vs. continuous), and the like.

In aspects, multiple applications of the high viscosity material forming the outer layer may be applied to the electrical assembly, so the outer layer, itself, is formed of multiple layers.

The thickness of the outer layer may be from about 300 μm to about 500 μm, in aspects from about 350 μm to about 450 μm.

The thickness of the resulting multi-layer coating, including both the inner layer(s) and the outer layer(s), may be from about 350 μm to about 700 μm, in aspects from about 400 μm to about 650 μm, in other aspects from about 450 μm to about 600 μm.

The resulting coating on the electrical assembly acts as a moisture barrier, so that moisture does not damage the underlying electrical assembly and its electrical components. The moisture barrier properties of the multi-layer conformal coating can be assessed by measuring the water vapor transmission rate (WVTR) using standard techniques, such as a MOCON test.

The multi-layer coating is thus able to protect the electrical components of the surgical devices and permits sterilization in harsh environments, including autoclaves and automated washes, and also protects the electrical components from moisture before and during use.

While the below description describes a multi-layer conformal coating on an electrical assembly of a surgical device, it is to be understood that the multi-layer conformal coatings of the present disclosure may be utilized with any surgical device possessing an electrical assembly, especially where the surgical device is to be subjected to sterilization, in aspects by the use of an autoclave, and the surgical device is to be reused.

Figure 1:
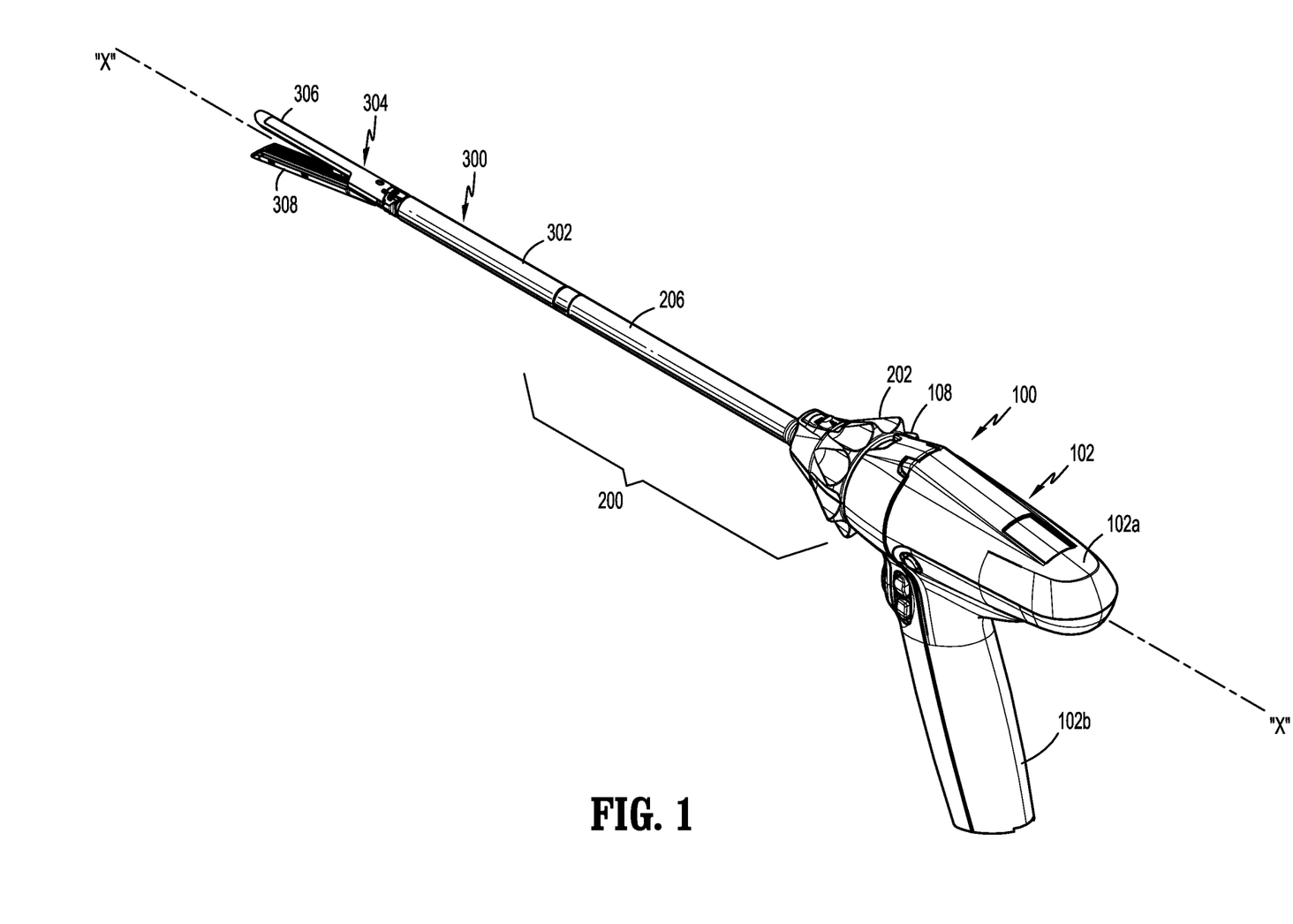
FIG. 1 is a perspective view of an adapter assembly in accordance with the present disclosure, interconnected between a handle of an exemplary electromechanical surgical device and an end effector assembly.

FIG. 1 depicts a surgical device 100 in the form of a powered hand held electromechanical instrument configured for selective attachment thereto of a plurality of different end effectors. Suitable end effectors are configured for actuation and manipulation by the powered hand held electromechanical surgical instrument. Surgical device 100 is configured for selective connection with an adapter assembly 200, and, in turn, adapter assembly 200 is configured for selective connection with a loading unit 300 and to actuate loading unit 300 (e.g., an end effector, multiple- or single-use loading unit, etc.).

In aspects, the surgical device 100 is a stapling device. Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of loading unit 300 of such a stapling device, as illustrated in FIG. 1.

Surgical device 100 includes a handle 102 including a printed circuit board ("PCB", not shown) and a drive mechanism (not shown) situated therein. The PCB is configured to control the various operations of surgical device 100. Handle 102 defines a cavity therein (not shown) for receipt of a rechargeable battery (not shown) therein. The battery is configured to supply power to any of the electrical components of surgical device 100.

Handle 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that is connected to or supporting adapter assembly 200 and/or loading unit 300.

Handle 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively move a tool assembly 304 of loading unit 300 (FIG. 1) relative to a proximal body portion 302 of loading unit 300, to rotate loading unit 300 about a longitudinal axis "X" (see FIG. 1) relative to handle 102, to move/approximate an anvil assembly 306 and a cartridge assembly 308 of loading unit 300 relative to one another, and/or to fire a stapling and cutting cartridge within cartridge assembly 308 of loading unit 300.

Figure 2:
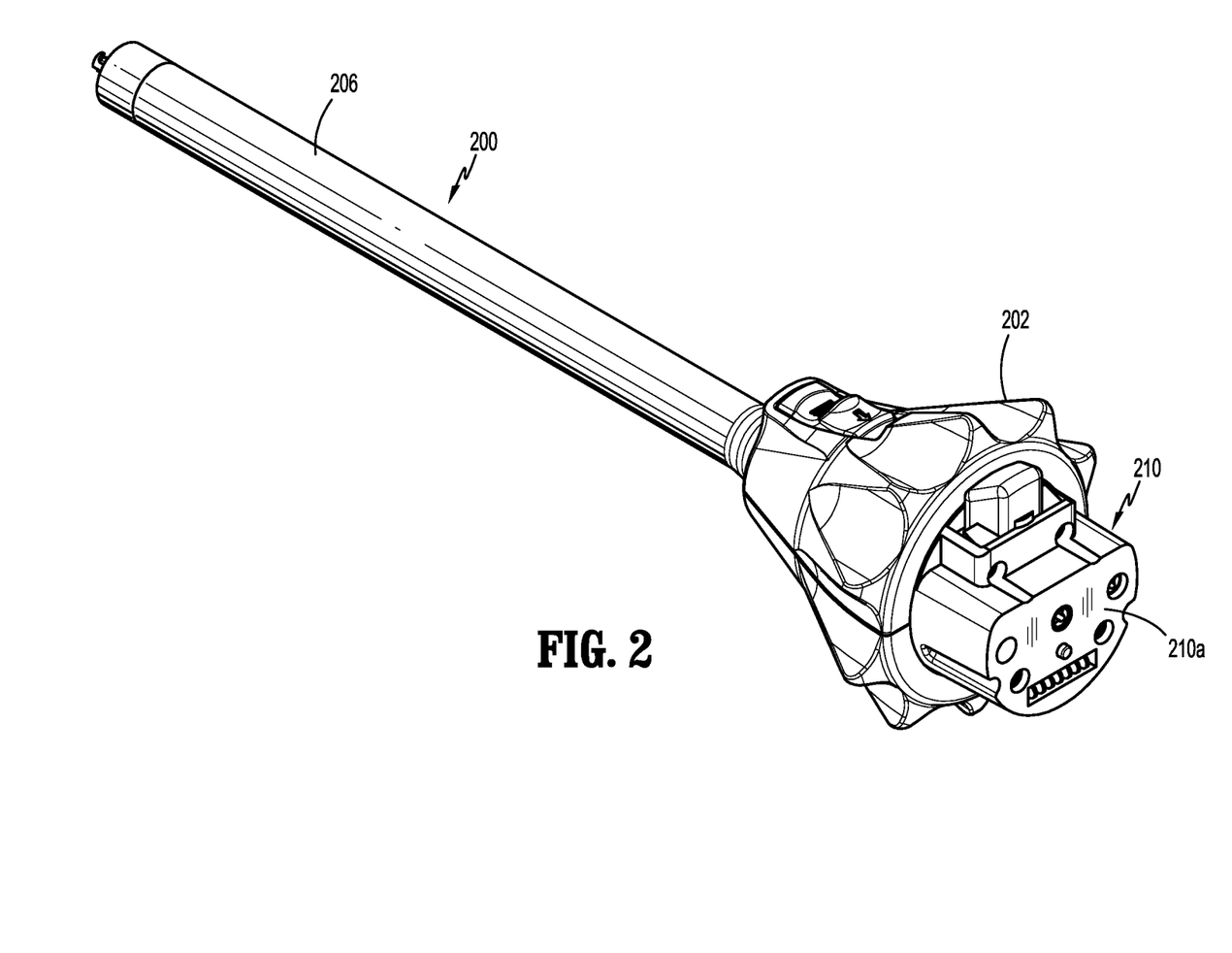
FIG. 2 is a rear, perspective view of the adapter assembly of FIG. 1.

As illustrated in FIGS. 1 and 2, handle 102 defines a connecting portion 108 configured to accept a corresponding drive coupling assembly 210 of adapter assembly 200. Specifically, connecting portion 108 of surgical device 100 has a recess (not shown) that receives a proximal cap 210a (FIG. 2) of drive coupling assembly 210 of adapter assembly 200 when adapter assembly 200 is mated to surgical device 100.

Figure 3:
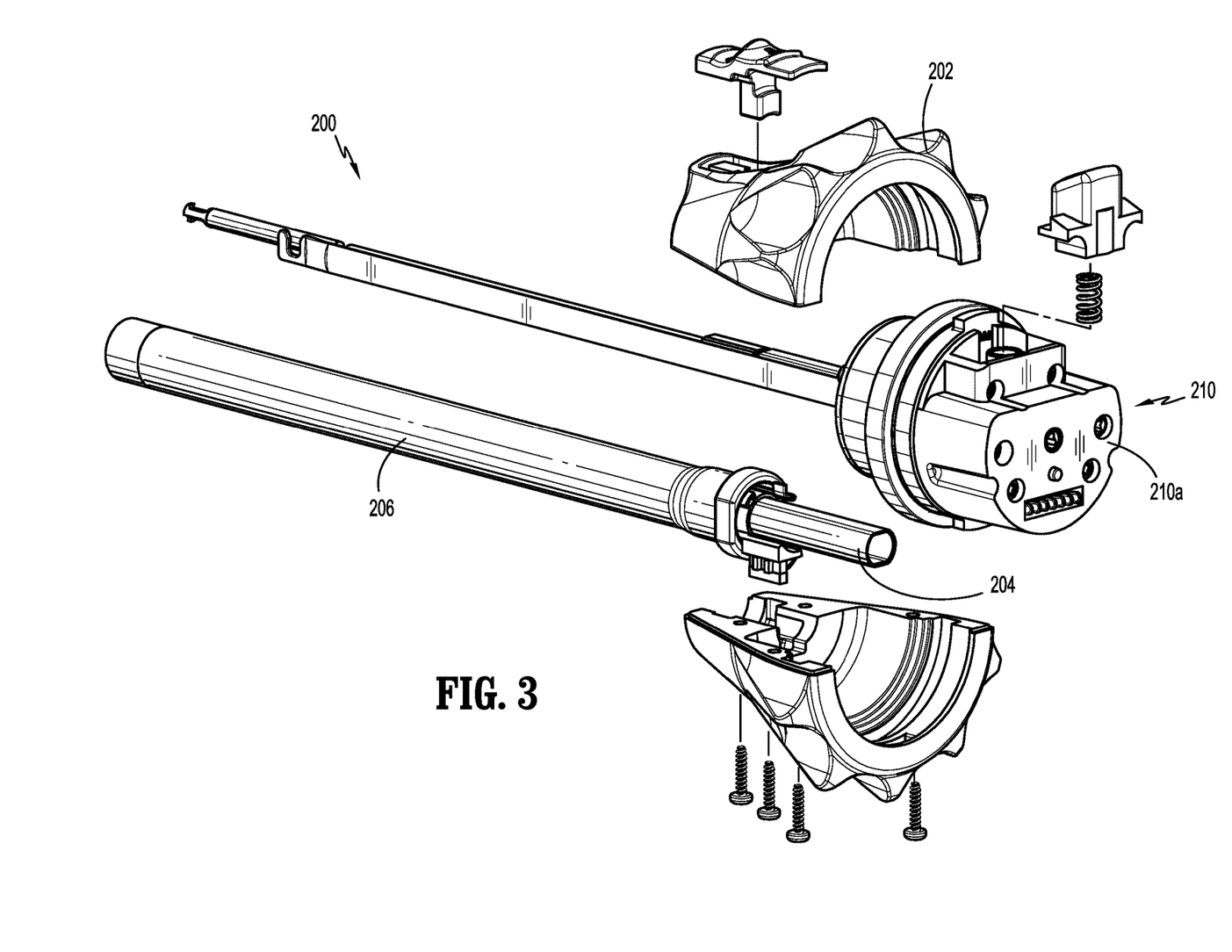
FIG. 3 is a rear, perspective view of the adapter assembly of FIG. 2, with some parts thereof separated.

Turning to FIGS. 1-3, adapter assembly 200 includes an outer knob housing 202 and an outer tube 206 extending from a distal portion of knob housing 202. Knob housing 202, outer tube 206, and inner tube 204 (FIG. 3) are configured and dimensioned to house the components of adapter assembly 200. Outer tube 206 is dimensioned for endoscopic insertion, in particular, so that outer tube is passable through a typical trocar port, cannula or the like. Knob housing 202 is configured and adapted to connect to connecting portion 108 of handle 102 of surgical device 100.

Adapter assembly 200 is configured to connect the handle 102 with the loading unit 300 and transmit electromechanical action between the handle 102 and the loading unit 300. In general, force/rotation transmitting/converting assemblies are included within adapter assembly 200 to effectuate articulation of loading unit 300; effectuate rotation of loading unit 300 about longitudinal axis "X" (FIG. 1); effectuate rotation of adapter assembly 200; effectuate closing, opening and firing of loading unit 300; effectuate closure of tool assembly 304 and firing of tool assembly 304 of loading unit 300; and effectuate articulation of tool assembly 304.

For a more detailed description of a suitable adapter assembly, including a detailed description of various internal components therein for transmitting/converting force and rotation, as well as electrical signals, see, e.g., U.S. patent application Ser. No. 14/550,183 (issued as U.S. Pat. No. 10,561,417), the entire disclosure of which is incorporated by reference herein.

Figure 4:
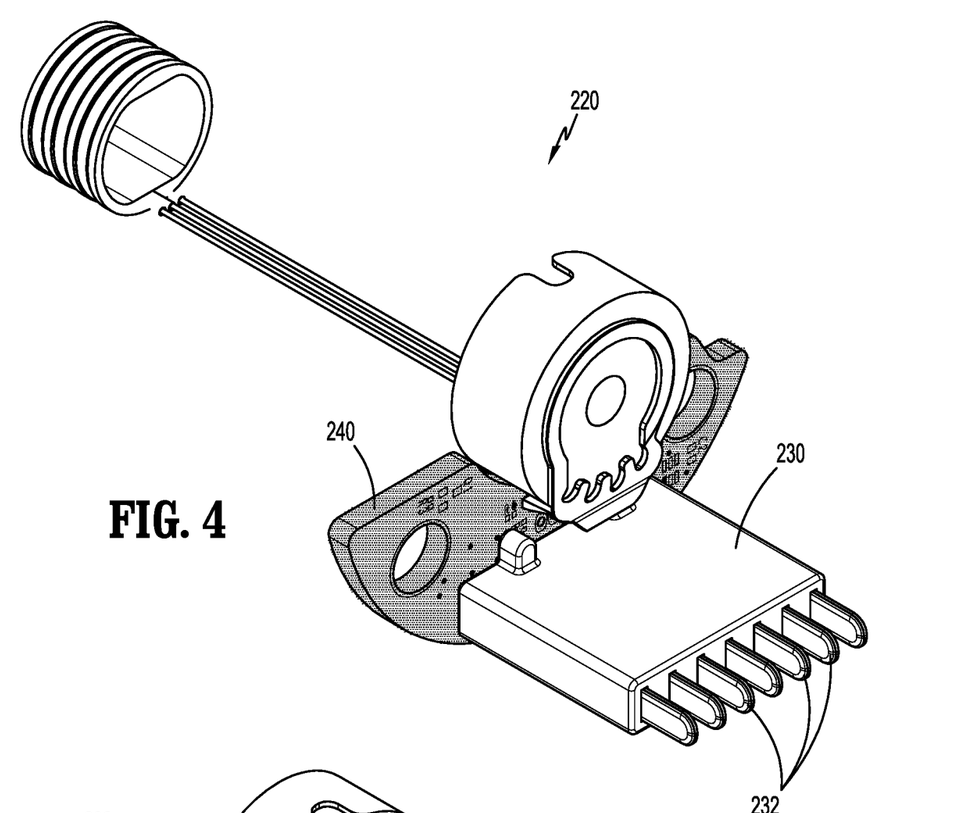
FIG. 4 is a perspective view of an electrical assembly included within the adapter assembly of FIG. 2.
Figure 5:
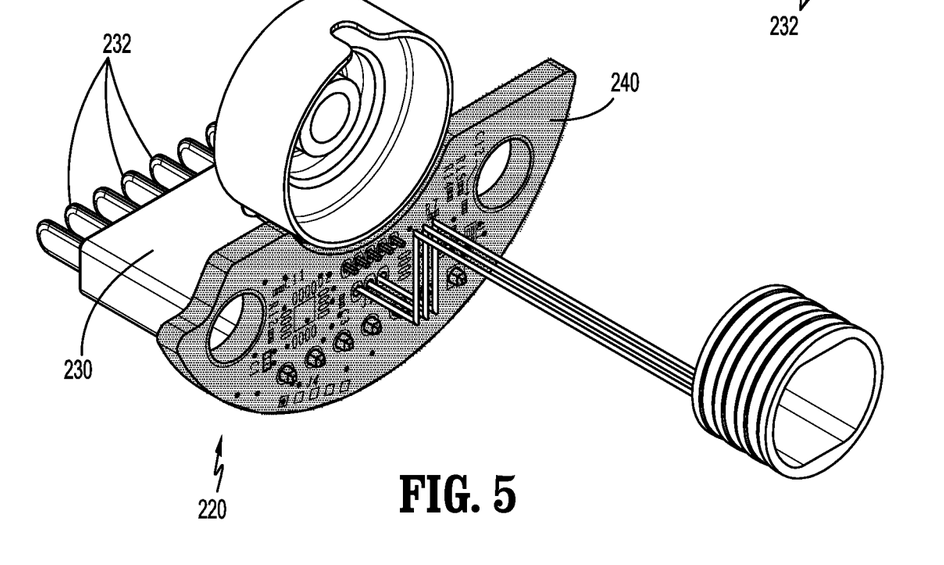
FIG. 5 is an alternate perspective view of the electrical assembly of FIG. 4.

With reference to FIGS. 4 and 5, adapter assembly 200 includes an electrical assembly 220 therein to assist in transmitting electrical signals between the handle 102 and the loading unit 300. Electrical assembly 220 includes an electrical plug 230 supported on a circuit board 240. The electrical plug 230 possesses a plurality of electrical contact pins 232 for electrical connection to a corresponding electrical receptacle (not shown) disposed in connecting portion 108 of surgical device 100. Electrical assembly 220 serves to allow for calibration and communication of life-cycle information to the PCB of surgical device 100 (not shown).

As shown in FIGS. 4 and 5, circuit board 240 has a multi-layer conformal coating of the disclosure thereon. As noted above, the multi-layer conformal coating is resistant to the heat, moisture and pressure used in sterilizing the surgical devices with an autoclave, permitting the sterilization and re-use of the disclosed surgical devices. The multi-layer conformal coating is very durable, permitting multiple sterilizations and uses of the surgical devices, thus prolonging the life of the surgical devices and making them much more economical when compared with single use devices.

Figure 6:
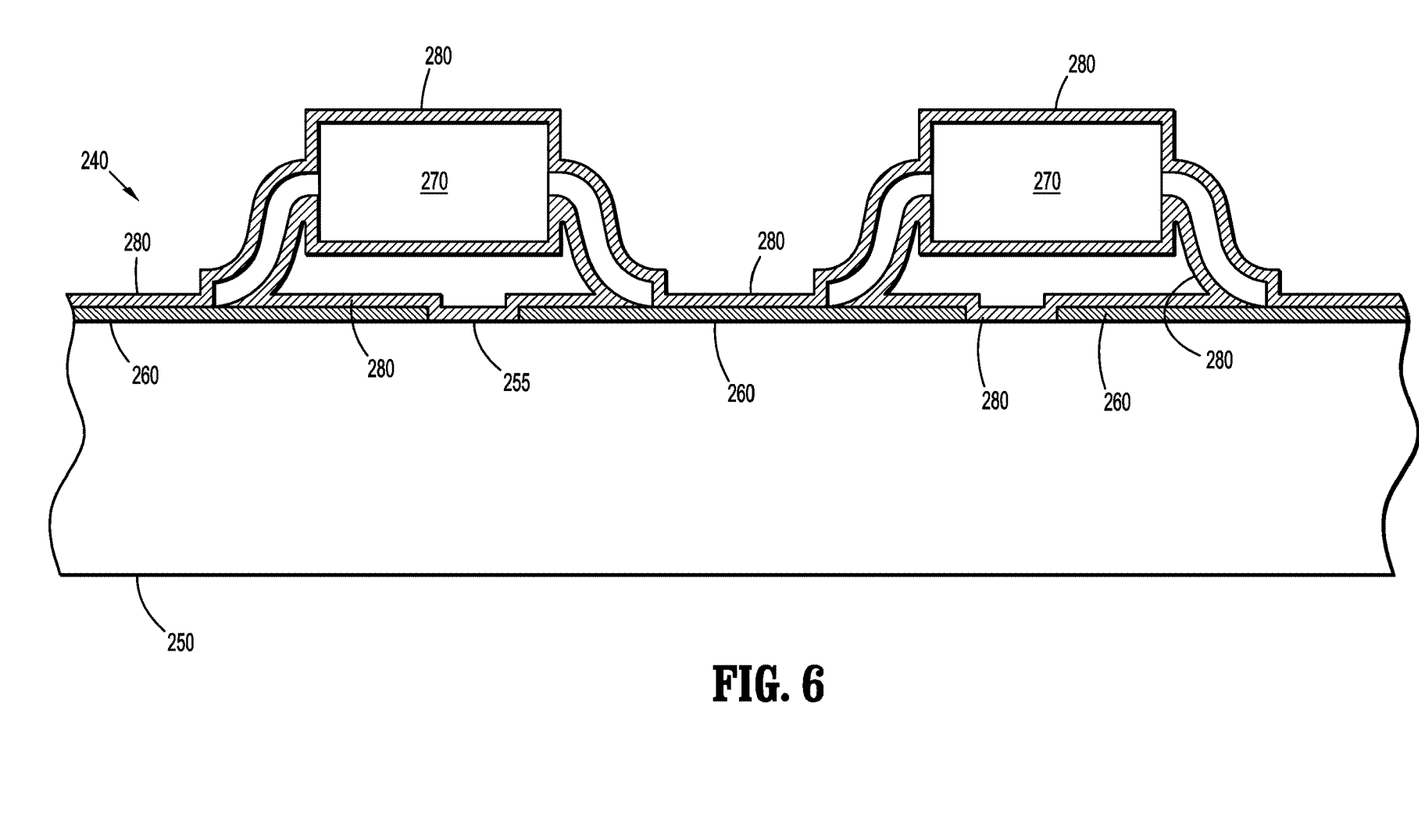
FIG. 6 shows an example of an electrical assembly which has a multi-layer conformal coating; and, FIG. 7 shows a cross section through the multi-layer conformal coating in FIG. 6.

FIG. 6 shows an example of a circuit board 240. The circuit board includes a substrate 250, a plurality of conductive tracks 260 present on least one surface of the substrate 250, and at least one electrical component 270 connected to at least one conductive track 260. The multi-layer conformal coating 280 covers the plurality of conductive tracks 260, the at least one electrical component 270 and the surface 255 of the substrate 250 on which the plurality of conductive tracks and the at least one electrical component are located.

Figure 7:
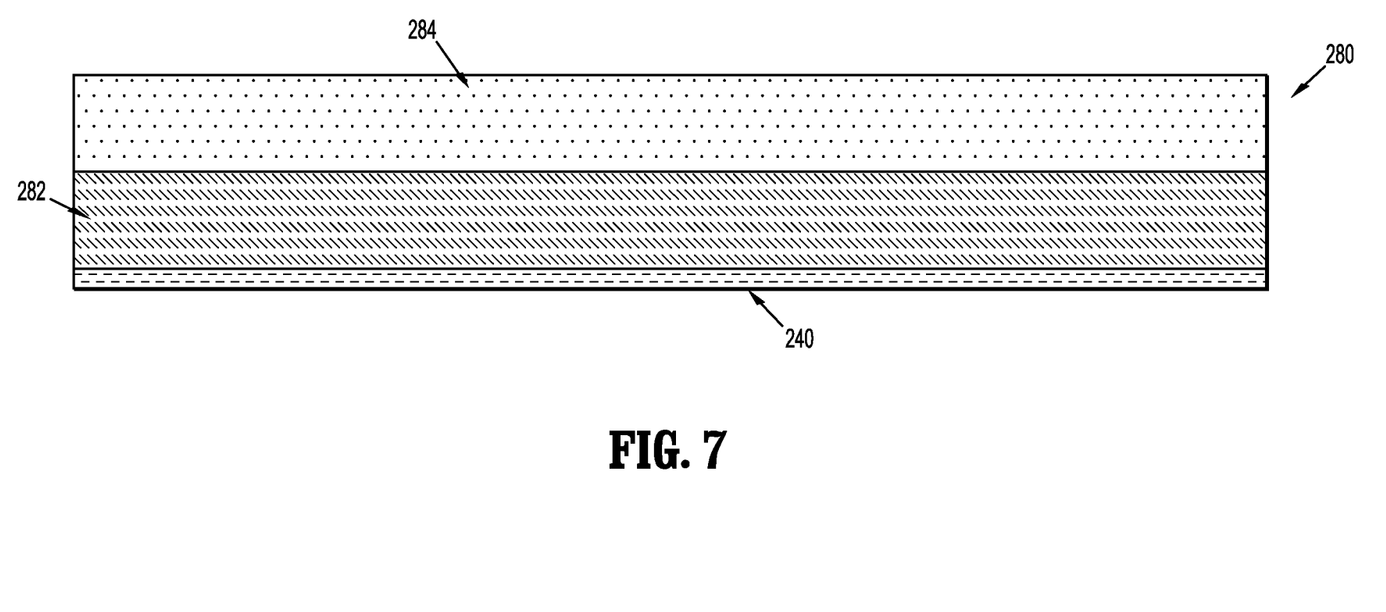

FIG. 7 shows a cross section through the multi-layer conformal coating 280 in FIG. 6. The multi-layer conformal coating includes an inner layer 282 which is in contact with the at least one surface of the circuit board 240, and an outer layer 284. This multi-layer conformal coating has two layers, and the boundary between the layers is discrete.

In operation, when a button of surgical device 100 is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter assembly 200 and/or loading unit 300.

Any of the other components of the medical device described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the disclosed surgical devices. Therefore, the above description should not be construed as limiting, but merely as exemplifications of aspects of the disclosure. Those skilled in the art will envision other modifications within the scope and spirit of the disclosure. For example, any and all features of one described aspect may be suitably incorporated into another aspect.

What is claimed is:

1. A hand-held electromechanical surgical device comprising:
    a housing;
    a loading unit; and
    an adapter assembly connecting the housing and the loading unit, the adapter assembly including an electrical assembly coated with a multi-layer conformal coating having at least one inner layer formed of a first material having a first viscosity and at least one outer layer formed of a second material having a second viscosity higher than the first viscosity,
    wherein the multi-layer conformal coating has a thickness from about 350 µm to about 700 µm.

2. The hand-held electromechanical surgical device according to claim 1, wherein the electrical assembly is a printed circuit board.

3. The hand-held electromechanical surgical device according to claim 2, wherein the printed circuit board includes a substrate, a plurality of conductive tracks on at least one surface of the substrate, and at least one electrical component connected to at least one conductive track.

4. The hand-held electromechanical surgical device according to claim 3, wherein the electrical component is a resistor, capacitor, transistor, diode, amplifier, relay, transformer, battery, fuse, integrated circuit, switch, LED, LED display, Piezo element, optoelectrical component, antenna, oscillator, or combinations thereof.

5. The hand-held electromechanical surgical device according to claim 3, wherein the multi-layer conformal coating covers the plurality of conductive tracks, the at least one electrical component, and the surface of the substrate on which the plurality of conductive tracks and the at least one electrical component are located.

6. The hand-held electromechanical surgical device according to claim 1, wherein the first material is a silicone having a first viscosity from about 195 cps to about 400 cps.

7. The hand-held electromechanical surgical device according to claim 1, wherein the inner layer has a thickness from about 50 µm to about 200 µm.

8. The hand-held electromechanical surgical device according to claim 1, wherein the second material is a room temperature vulcanizing silicone having a second viscosity from about 3000 cps to about 10000 cps.

9. The hand-held electromechanical surgical device according to claim 1, wherein the outer layer has a thickness from about 300 µm to about 500 µm.

10. A hand-held electromechanical surgical device comprising:
    a housing;
    a loading unit;
    an adapter assembly connecting the housing and the loading unit, the adapter assembly including an electrical assembly, the electrical assembly including a printed circuit board including a substrate, a plurality of conductive tracks on at least one surface of the substrate, and at least one electrical component connected to at least one conductive track; and
    a multi-layer conformal coating covering the plurality of conductive tracks, the at least one electrical component, and the surface of the substrate on which the plurality of conductive tracks and the at least one electrical component are located,
    wherein the multi-layer conformal coating has a thickness from about 350 µm to about 700 µm.

11. The hand-held electromechanical surgical device according to claim 10, wherein the electrical component is a resistor, capacitor, transistor, diode, amplifier, relay, transformer, battery, fuse, integrated circuit, switch, LED, LED display, Piezo element, optoelectrical component, antenna, oscillator, or combinations thereof.

12. The hand-held electromechanical surgical device according to claim 10, wherein the multi-layer conformal coating has at least one inner layer formed of a first material including a silicone having a viscosity from about 195 cps to about 400 cps, and at least one outer layer formed of a second material including a room temperature vulcanizing silicone having a viscosity from about 3000 cps to about 10000 cps.

13. The hand-held electromechanical surgical device according to claim 12, wherein the inner layer has a thickness from about 50 µm to about 200 µm, and the outer layer has a thickness from about 300 µm to about 500 µm.

14. An adapter assembly for connecting a surgical loading unit configured to perform a function with a handle of a surgical device that is configured to actuate the loading unit, the adapter assembly comprising:

an electrical assembly including a printed circuit board, the printed circuit board including a substrate, a plurality of conductive tracks on at least one surface of the substrate, and at least one electrical component connected to at least one conductive track; and a multi-layer conformal coating covering the plurality of conductive tracks, the at least one electrical component, and the surface of the substrate on which the plurality of conductive tracks and the at least one electrical component are located, wherein the multi-layer conformal coating has a thickness from about 350 μm to about 700 μm.

15. The adapter assembly according to claim 14, wherein the electrical component is a resistor, capacitor, transistor, diode, amplifier, relay, transformer, battery, fuse, integrated circuit, switch, LED, LED display, Piezo element, optoelectrical component, antenna, oscillator, or combinations thereof.

16. The adapter assembly according to claim 14, wherein the multi-layer conformal coating has at least one inner layer formed of a first material having a first viscosity and at least one outer layer formed of a second material having a second viscosity higher than the first viscosity.

17. The adapter assembly according to claim 16, wherein the first material is a silicone having a viscosity from about 195 cps to about 400 cps.

18. The adapter assembly according to claim 16, wherein the inner layer has a thickness from about 50 μm to about 200 μm.

19. The adapter assembly according to claim 16, wherein the second material is a room temperature vulcanizing silicone having a viscosity from about 3000 cps to about 10000 cps.

20. The adapter assembly according to claim 16, wherein the outer layer has a thickness from about 300 μm to about 500 μm.

* * * * *